United States Patent
Iizuka et al.

(10) Patent No.: US 9,117,008 B2
(45) Date of Patent: Aug. 25, 2015

(54) DISPLAY APPARATUS AND DISPLAY METHOD FOR DISPLAYING THE RADIOGRAPHING RANGE OF A HUMAN BODY TO BE EXAMINED

(75) Inventors: Yoshio Iizuka, Yokohama (JP); Hidehiko Morinaga, Tokyo (JP); Akira Yoshino, Tokyo (JP); Maiko Sato, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 768 days.

(21) Appl. No.: 13/216,570

(22) Filed: Aug. 24, 2011

(65) Prior Publication Data

US 2012/0050330 A1 Mar. 1, 2012

(30) Foreign Application Priority Data

Aug. 31, 2010 (JP) ................................. 2010-193751

(51) Int. Cl.
*G06F 19/00* (2011.01)
*A61B 6/00* (2006.01)
*G06T 11/60* (2006.01)
*H04N 5/272* (2006.01)

(52) U.S. Cl.
CPC ............ *G06F 19/321* (2013.01); *A61B 6/5235* (2013.01); *A61B 6/5247* (2013.01); *G06F 19/3487* (2013.01); *G06T 11/60* (2013.01); *G09G 2340/10* (2013.01); *H04N 5/272* (2013.01)

(58) Field of Classification Search
CPC ........... A61B 8/13; A61B 8/463; A61B 8/469
See application file for complete search history.

(56) References Cited

U.S. PATENT DOCUMENTS

| | | | |
|---|---|---|---|
| 7,088,798 B2 | 8/2006 | Chen et al. | |
| 7,603,155 B2 | 10/2009 | Jensen | |
| 7,965,907 B2 | 6/2011 | Takekoshi | |
| 8,199,876 B2 | 6/2012 | Graumann et al. | 378/63 |
| 8,340,241 B2 | 12/2012 | Adachi et al. | |
| 2004/0172292 A1 | 9/2004 | Takekoshi et al. | |
| 2006/0072700 A1 | 4/2006 | Chen et al. | |
| 2006/0293582 A1 | 12/2006 | Jensen | |
| 2007/0201610 A1 | 8/2007 | Adachi et al. | |

(Continued)

FOREIGN PATENT DOCUMENTS

| | | |
|---|---|---|
| CN | 1503185 A | 6/2004 |
| CN | 1754508 A | 4/2006 |

(Continued)

OTHER PUBLICATIONS

Office Action dated Jun. 1, 2012, issued in counterpart German Patent Application No. 102011081813.8, with translation.

(Continued)

*Primary Examiner* — Maurice L McDowell, Jr.
*Assistant Examiner* — Donna J Ricks
(74) *Attorney, Agent, or Firm* — Fitzpatrick, Cella, Harper & Scinto

(57) ABSTRACT

A display apparatus comprises an obtaining unit that obtains information associated with a human body to be examined, a forming unit that forms, based on information on a radiographing range of a radiographing apparatus with respect to the human body to be examined included in the obtained information, a graphic showing the radiographing range of the radiographing apparatus onto a body diagram of the human body to be examined; and a display control unit that controls a display unit to display the formed graphic.

6 Claims, 6 Drawing Sheets

(56) References Cited

U.S. PATENT DOCUMENTS

| | | |
|---|---|---|
| 2009/0022378 A1 | 1/2009 | Nemoto |
| 2009/0054755 A1 | 2/2009 | Shiibashi |
| 2009/0141958 A1 | 6/2009 | Graumann et al. |
| 2011/0091082 A1 | 4/2011 | Takekoshi et al. |
| 2011/0228995 A1* | 9/2011 | Batman et al. ................ 382/128 |
| 2012/0069048 A1 | 3/2012 | Takekoshi et al. |

FOREIGN PATENT DOCUMENTS

| | | | | |
|---|---|---|---|---|
| CN | 101028197 A | 9/2007 | | |
| CN | 101155551 A | 4/2008 | | |
| CN | 101395630 A | 3/2009 | | |
| DE | 10 2005 062 582 A | 7/2007 | | |
| DE | 102005062582 A1 | 7/2007 | | |
| DE | EP1990765 A1 * | 12/2008 | ............ | G06Q 50/00 |
| EP | 1 872 721 A1 | 1/2008 | | |
| EP | 1872721 | 1/2008 | | |
| EP | 1990765 | 11/2008 | | |
| JP | 406169907 A * | 6/1994 | ............... | A61B 6/00 |
| JP | 2005-080969 A | 3/2005 | | |
| JP | 2005-319179 A | 11/2005 | | |
| JP | 2006326298 A | 12/2006 | | |
| JP | 2008-264167 | 11/2008 | | |
| JP | 2008-264167 A | 11/2008 | | |
| JP | 2008264167 * | 11/2008 | ............... | A61B 5/00 |
| JP | 2010/057684 A | 3/2010 | | |

OTHER PUBLICATIONS

Korean Office Action issued in counterpart application No. 10-2013-0136797 dated Sep. 29, 2014, along with its English-language translation—8 pages.

Chinese Office Action issued in counterpart application No. 201110258729.5 dated May 20, 2014, along with its English-language translation—7 pages.

* cited by examiner

FIG. 2

| READING STATUS | RADIO-GRAPHING DAY | INSPECTION ID | SERIES NO. | THE NUMBER OF IMAGES | PATIENT ID | MODALITY | RADIO-GRAPHING REGION | REQUESTING DEPARTMENT |
|---|---|---|---|---|---|---|---|---|
| DECIDED | 07/01/2010 | 070101 | 4 | 640 | 00232 | MRI | HEAD | BRAIN SURGERY |
| DECIDED | 07/01/2010 | 070102 | 4 | 723 | 00167 | CONTRAST CT | UPPER ABDOMINAL | CIRCULATORY ORGAN |
| DECIDED | 07/01/2010 | 070103 | 1 | 231 | 00244 | MRI | MAMMA | MAMMARY |
| READ | 07/01/2010 | 070104 | 2 | 384 | 00129 | CONTRAST CT | CHEST ABDOMINAL | RESPIRATORY MEDICINE |
| READ | 07/01/2010 | 070105 | 3 | 678 | 00084 | MRI | HEAD | BRAIN SURGERY |
| READ | 07/01/2010 | 070106 | 2 | 434 | 00063 | CT | CHEST ABDOMINAL | CIRCULATORY ORGAN |
| READ | 07/01/2010 | 070107 | 1 | 265 | 00271 | MRI | MAMMA | MAMMARY |
| UNREAD | 07/01/2010 | 070108 | 2 | 394 | 00015 | MRI | CHEST | RESPIRATORY MEDICINE |
| UNREAD | 07/01/2010 | 070109 | 2 | 417 | 00342 | CT | CHEST | RESPIRATORY MEDICINE |
| UNREAD | 07/01/2010 | 070110 | 2 | 528 | 00410 | CONTRAST CT | CHEST ABDOMINAL | CIRCULATORY ORGAN |

210 MEDICAL IMAGE LIST
I1 MEDICAL IMAGE, F1 GRAPHIC
220 GRAPHIC INFORMATION DISPLAY AREA
F1 GRAPHIC
H1 GRAPHIC
M1 SCALE

DISPLAY APPARATUS AND DISPLAY METHOD FOR DISPLAYING THE RADIOGRAPHING RANGE OF A HUMAN BODY TO BE EXAMINED

BACKGROUND OF THE INVENTION

1. Field of the Invention

The present invention relates to a technique for displaying the radiographing range of a human body to be examined.

2. Description of the Related Art

A list display apparatus of a medical image in the related art displays list display items (radiograph information, attribute information of a patient, attribute information of the medical image) as a character string. Ordinarily, the list display items regarding the medical image obtained by one inspection (radiographing) are displayed on one row of a list.

Japanese Patent Application Laid-Open No. 2008-264167 discloses such a technique that when the user selects one medical image on a medical image list displayed by a character string, a diagram showing a radiographing region and an image type of the medical image is illustrated on a body diagram of a human body. Thus, the user can easily discriminate the radiographing region and image type of the selected medical image.

SUMMARY OF THE INVENTION

However, according to the technique disclosed in the foregoing reference, since the method of illustrating the radiographing region by a region image of the model of the human body is used, it is difficult to illustrate a radiographing region which does not coincide with a prepared region image. Also, according to the technique disclosed in the above reference, at which posture the patient was radiographed, that is, the posture of the patient to a radiographing apparatus or a gravity direction cannot be shown. Further, there is a case where a plurality of medical images of the same patient exist such as case where different inspections (radiographing using different modalities) were performed to the same patient, case where the radiographing was performed a plurality of number of times on a plurality of days, or the like. However, according to the related art, such a process that a fact that there are a plurality of medical images of the same patient is shown on a diagram and attribute information of those plurality of medical images is also shown on the diagram simultaneously with the medical images cannot be realized. Therefore, the information which can be easily discriminated by the related art is limited. There is such a problem that the user cannot easily discriminate the useful attribute information such as accurate radiographing region of the patient, posture upon radiographing of the patient, and attribute information of a plurality of medical images of the same patient. The invention is made in consideration of such problems and it is an object of the invention to provide an apparatus which can solve the above problems.

In order to solve the problems discussed above, the present invention provides with a display apparatus comprising: an obtaining unit that obtains information associated with a human body to be examined; a forming unit that forms, based on information on a radiographing range of a radiographing apparatus with respect to the human body to be examined included in the obtained information, a graphic showing the radiographing range of the radiographing apparatus onto a body diagram of the human body to be examined; and a display control unit that controls a display unit to display the formed graphic.

According to the display apparatus of the invention, the radiographing range of a human body to be examined can be easily discriminated.

Further features of the present invention will become apparent from the following description of exemplary embodiments with reference to the attached drawings.

BRIEF DESCRIPTION OF THE DRAWINGS

FIG. 2 is a diagram illustrating a display example of a first display screen of the display apparatus according to the first embodiment.

DESCRIPTION OF THE EMBODIMENTS

Exemplary embodiments of a display apparatus according to the invention and its control method will be described hereinbelow with reference to the drawings. A scope of the invention is not limited to examples illustrated in the diagrams.

First Embodiment

Figure 1:
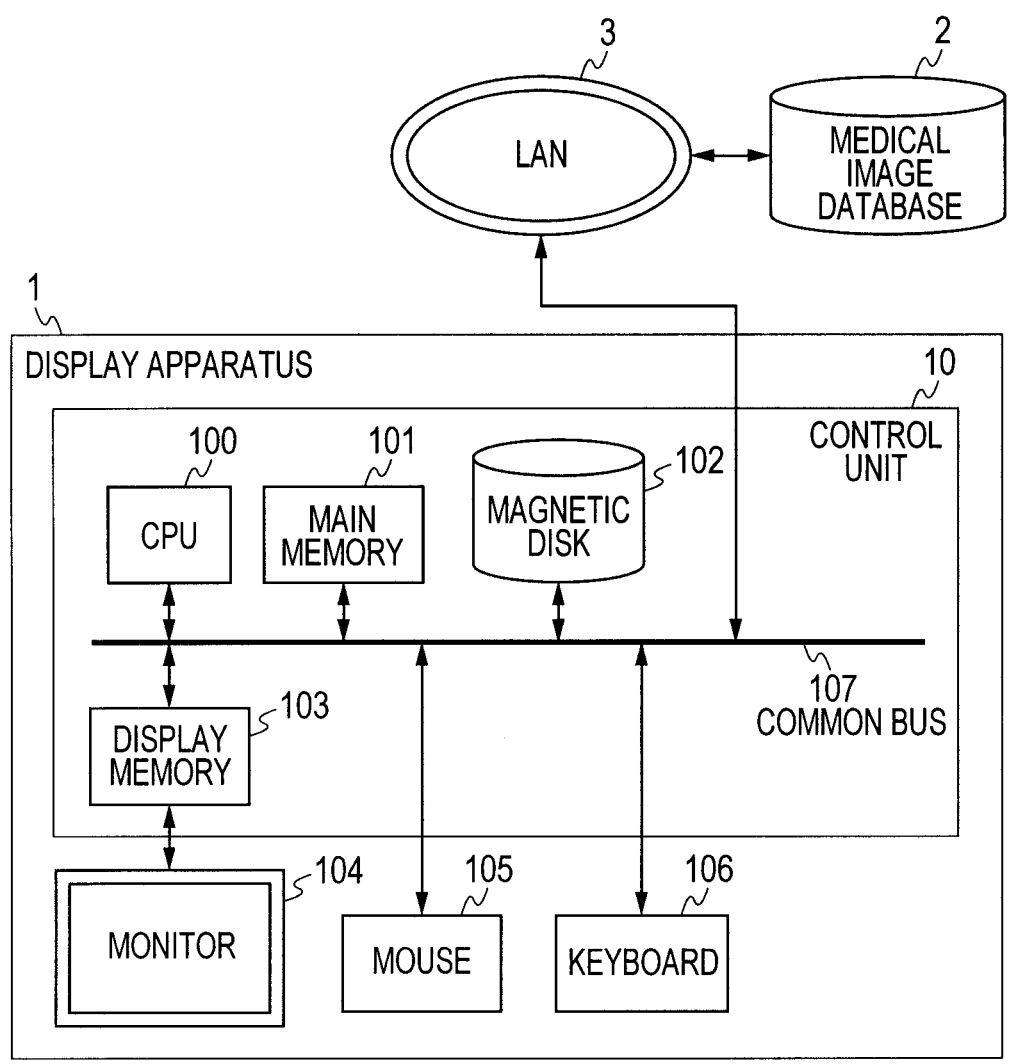
FIG. 1 is a diagram illustrating a constructional example of a display apparatus according to the first and second embodiments.

FIG. 1 is a diagram illustrating a constructional example of a display apparatus according to the first embodiment. A display apparatus 1 has a control unit 10, a monitor 104, a mouse 105, and a keyboard 106. The control unit 10 has a central processing unit (CPU) 100, a main memory 101, a magnetic disk 102, and a display memory 103. The CPU 100 executes a program stored in the main memory 101, so that various kinds of control such as communication with a medical image database 2, whole control of the display apparatus 1, and the like are executed.

The CPU 100 controls mainly the operation of each component element of the display apparatus 1. The main memory 101 stores a control program which is executed by the CPU 100 and provides a work area at the time when the program is executed by the CPU 100. The magnetic disk 102 stores an operating system (OS), device drives of peripheral devices, various kinds of application software including a program for executing a diagnosis supporting process, which will be described hereinafter, and the like. The display memory 103 temporarily stores display data for the monitor 104. The monitor 104 is, for example, a CRT monitor, a liquid crystal monitor, or the like and displays an image based on data from the display memory 103. The mouse 105 and keyboard 106 are used for the user (doctor) to perform a pointing input and an input of characters or the like, respectively. The above component elements are connected by a common bus 107 so that they can communicate with each other.

In the embodiment, the display apparatus 1 can read out image data from the medical image database 2 through a LAN (Local Area Network) 3. An existing PACS (Picture Archiving and Communication System) can be used as a medical image database 2. It is also possible to construct in such a manner that an external storage device such as FDD, HDD, CD drive, DVD drive, MO drive, ZIP drive, or the like is connected to the display apparatus 1 and the image data is read out of those drives.

The above apparatus construction can be realized by using a general computer and its peripheral devices. A control procedure of the display apparatus according to the invention, which will be described hereinafter by using FIG. 5, can be realized as a program which is executed on the computer.

As types of medical images, there are a simple X-ray image, an X-ray CT image, an MRI image, a PET image, an SPECT image, an ultrasonic image, and the like. Generally, the medical image is stored as a file (DICOM file) which conforms with the international standard specifications regarding the communication and storage of medical images called a DICOM standard. Various kinds of information such as radiograph information, attribute information of the patient, attribute information of the medical image, and the like has been recorded in the former half portion (header portion) of the DICOM file. A part of those information can be used as list display items. Or, the radiograph information, attribute information of the patient, attribute information of the medical image, and the like can be received through the LAN 3 from a radiology information system (RIS) (not shown) serving as a system for instructing a creation and storage of the DICOM file.

FIG. 2 is a diagram illustrating a display example of a first display screen of the display apparatus according to the first embodiment. In the diagram, list display items are displayed as a character string on a medical image list 210. In the example of the drawing, the list display items regarding the medical image obtained by one inspection (radiographing) are displayed in each row of the list. In the example of the drawing, a reading status, a radiographing day, an inspection day, a series number, the number of images, a patient ID, a modality, a radiographing region, and a requesting department are displayed as list display items. The reading status indicates a progressing situation of an image diagnosis. The series number indicates the number of bundles of a plurality of slice images which are obtained by one radiographing of a CT or an MRI. The number of images indicates the total number of images of all series radiographed by one inspection. The modality indicates a type of radiographing apparatus and the presence or absence of use of a contrast medium. As other items, information such as name of the patient, name of the image diagnosis doctor, and the like may be displayed.

A graphic H1 serving as a body diagram of a human body, a graphic F1 showing predetermined attribute information A1 of a medical image I1, and a scale M1 showing a size of patient and a size of radiographing range are displayed in a graphic information display area 220. The graphic H1 is used as meaning showing the information for graphically displaying the human body. An image or a symbol may be used in place of the graphic. Similarly, the graphic F1 is used as meaning showing the information for graphically displaying the predetermined attribute information A1 of the medical image I1. An image or a symbol may be used in place of the graphic. It is sufficient to display the scale M1 in accordance with necessity. The medical image I1 is a medical image selected on the medical image list 210 by the user. In the example of the drawing, the radiographing region is used as predetermined attribute information A1 of the medical image.

The graphic F1 is displayed as a rectangle showing the radiographing range at a position properly showing the radiographing region of the medical image I1. The graphic F1 is arranged at a proper position for the graphic H1. Therefore, if more accurate radiographing position information can be used in place of the radiographing region, the graphic F1 can be displayed by the accurate rectangular size at the accurate radiographing position. For example, there is a case where the accurate radiographing range along a coordinate axis in which a collarbone is set to a reference point (position 0 mm) and the direction orienting from the head toward the feet is set to the + direction is disclosed on a mm unit basis in the header portion of the DICOM file of a CT image of a chest region. By reading out such accurate position information from the header portion of the DICOM file and using it as attribute information A1, the graphic F1 can be displayed at the more accurate position for the graphic H1. Further, if the height of patient can be read out of the header portion of the DICOM file, a size of scale M1 (notch width of the scale) can be properly displayed to the size of graphic F1. Or, contrarily, the size of scale M1 is fixed and the size of graphic F1 can be properly adjusted and displayed.

Figure 3:
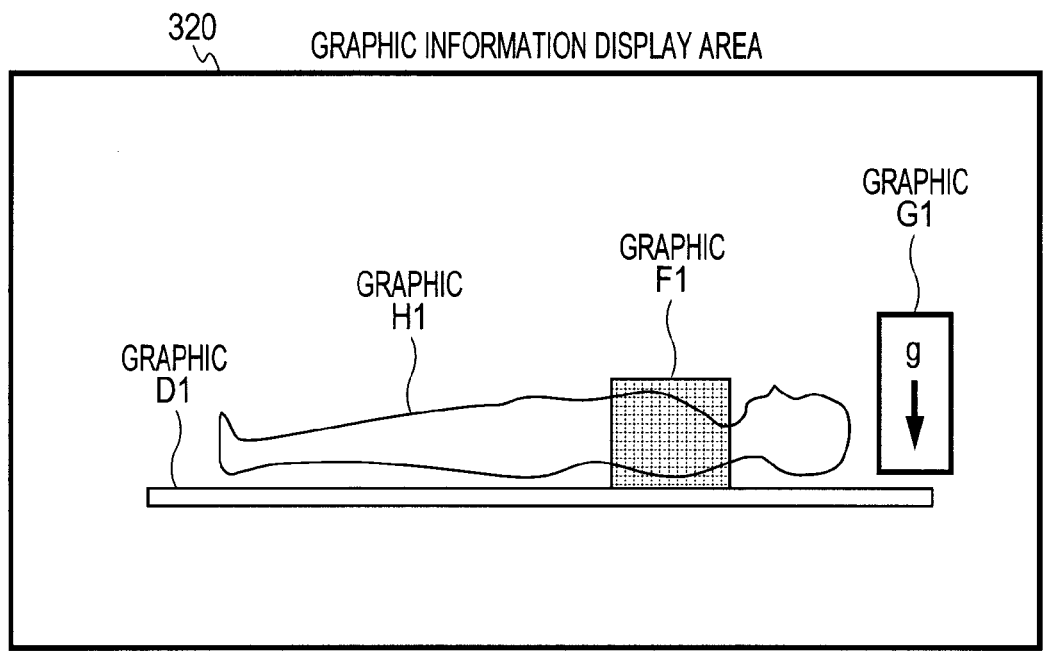
FIG. 3 is a diagram illustrating a display example of a second display screen of the display apparatus according to the first embodiment.

FIG. 3 is a diagram illustrating a display example of a second display screen of the display apparatus according to the first embodiment. However, since a medical image list is similar to that of the example illustrated in FIG. 2, its display is omitted and only a graphic information display area 320 is displayed.

In the example of FIG. 3, a case where the modality which has radiographed the medical image I1 is a radiographing apparatus having a bed is presumed. In the drawing, the graphic H1 serving as a body diagram of a human body shows the posture of the patient at the time of radiographing the medical image I1 to a graphic D1 showing the bed of the radiographing apparatus. The posture of the patient is preliminarily obtained by a predetermined method. For example, if information showing the posture of the patient has been stored in the medical image database 2 or the radiology information system (RIS) (not shown), the information showing the posture of the patient can be obtained from those apparatuses through the LAN 3. Or, even when the information showing the posture of the patient cannot be directly obtained, there is a case where if the modality and the radiographing region are known, whether the patient is in a face-down position or a face-up position can be discriminated. For example, if the modality is a CT or PET, the posture of the patient is ordinarily the face-up position. For example, if the modality is an MRI and the radiographing region is a mamma, the posture of the patient is ordinarily the face-down position. Therefore, if the accurate information showing the posture of the patient cannot be obtained, it is sufficient to discriminate the general posture of the patient from other attribute information such as modality, radiographing region, or the like. Further, the scale M1 may be displayed in accordance with the necessity in a manner similar to FIG. 2.

A graphic G1 indicates a gravity direction. In the example of the drawing, since the patient lies on the bed, it is known that the gravity direction is a direction orienting from the patient toward the bed. The graphic F1 showing the radiographing region as attribute information A1 of the medical image I1 is displayed as a rectangle showing the radiographing range at the position properly showing the radiographing region of the medical image I1.

Figure 4:
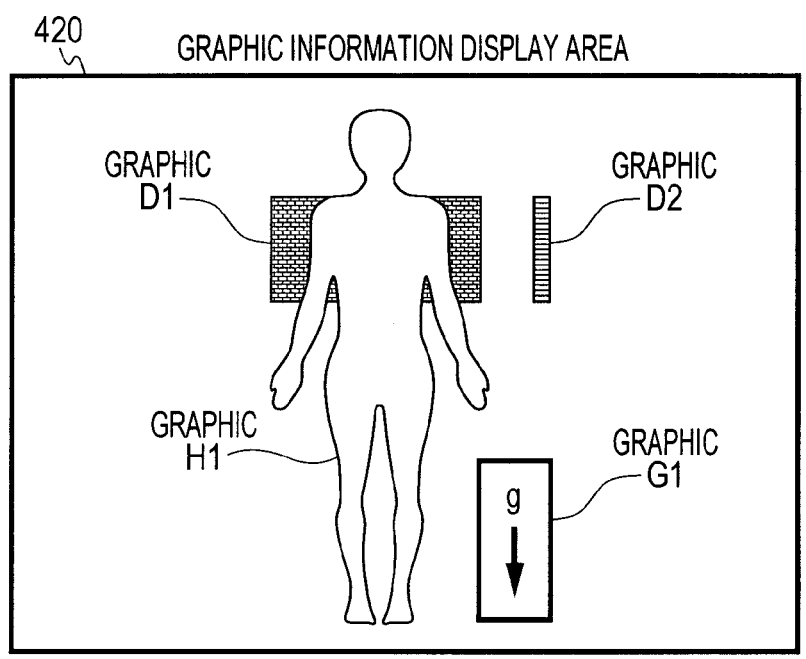
FIG. 4 is a diagram illustrating a display example of a third display screen of the display apparatus according to the first embodiment.

FIG. 4 is a diagram illustrating a display example of a third display screen of the display apparatus according to the first embodiment. In a manner similar to FIG. 3, a display of a medical image list is omitted and only a graphic information display area 420 is displayed.

In the example of FIG. 4, a case where medical images I1 and I2 of the same patient were radiographed by a radiographing apparatus (for example, a flat panel type X-ray radiographing apparatus) which can radiograph from different directions is presumed. In the diagram, the graphic H1 serving as a body diagram of a human body shows the posture of the patient at the time of radiographing the medical images I1 and I2 to the gravity direction shown by graphic G1. Graphics D1 and D2 corresponding to radiographing directions B1 and B2 (not shown) of the medical images I1 and I2 are displayed so as to show a layout of the radiographing apparatus to the patient illustrated by the graphic H1. The layout of the radiographing apparatus to the patient and the gravity direction are preliminarily obtained by a predetermined method. For example, if information showing the layout of the radiographing apparatus to the patient and the gravity direction has been stored in the medical image database 2 or RIS (not shown), the necessary information can be obtained from those apparatuses through the LAN 3. Further, the scale M1 may be displayed in accordance with the necessity in a manner similar to FIG. 2.

Figure 5:
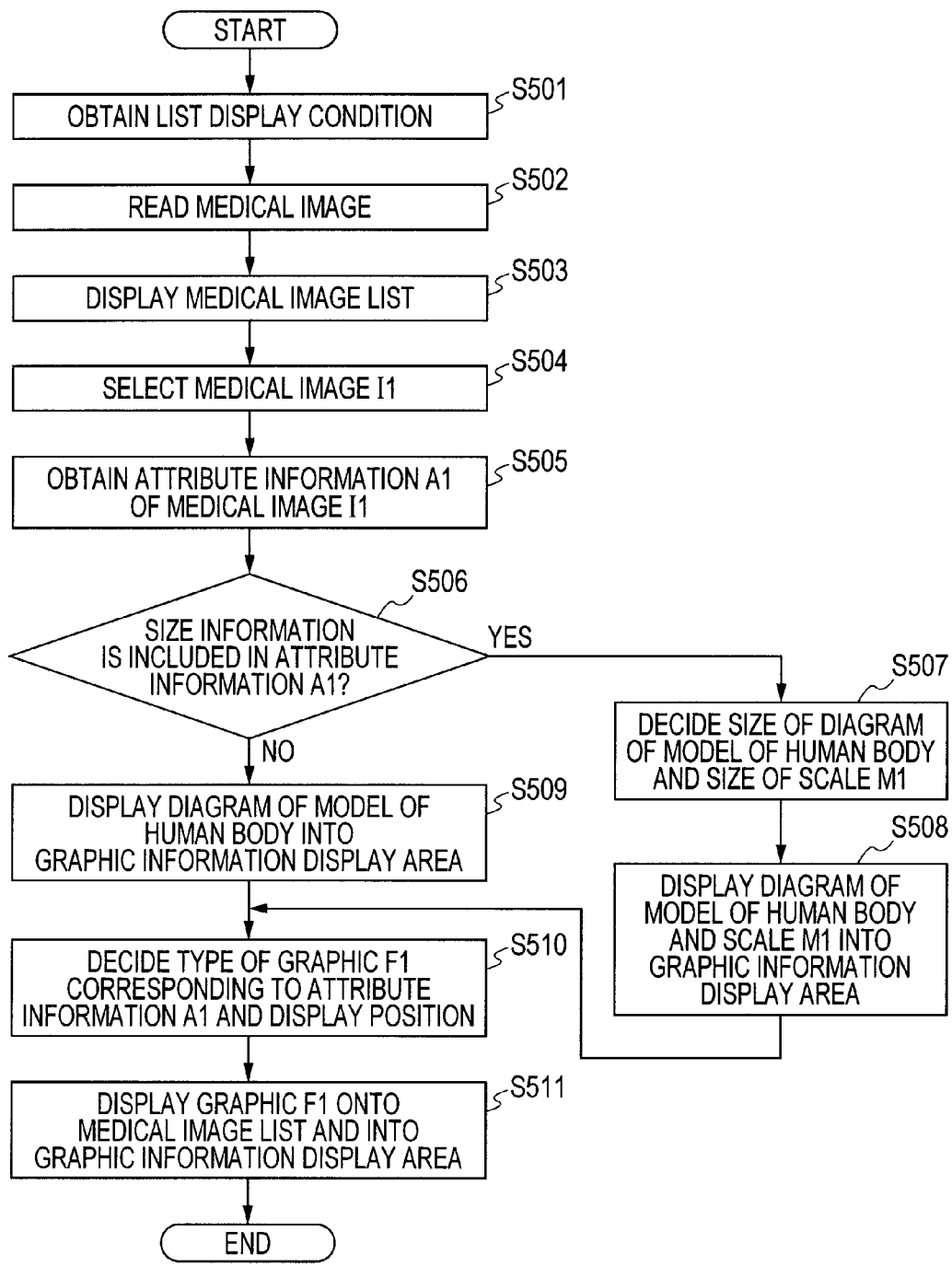
FIG. 5 is a flowchart illustrating a control procedure of the display apparatus according to the first embodiment.

FIG. 5 is a flowchart illustrating a control procedure of the display apparatus according to the first embodiment.

In step S501, a list display condition of the medical image list is obtained. The list display condition is a condition adapted to decide a display method of the medical image list 210 and the graphic information display area 220 illustrated as an example in FIG. 2. By changing the list display condition in accordance with an instruction of the user, types of list display items which are displayed on the medical image list 210, a type of graphic F1 which is displayed in the graphic information display area 220, a display position, a display size, and the like can be changed. In step S501, the list display conditions which have previously been stored in the magnetic disk 102 are read out into the main memory 101, thereby obtaining initial values of the list display conditions. In step S501, further, when the instruction of the user is input from the mouse 105 or the keyboard 106, the list display condition is changed in accordance with the instruction of the user and the list display condition after the change is stored into the main memory 101.

In step S502, the information (list display items) necessary to display the medical image list is read out of the medical image database 2 through the LAN 3 in accordance with the list display condition. In step S503, the information read out in step S502 is edited into a table format and, thereafter, written into the display memory 103, thereby displaying the medical image list onto the monitor 104. In step S504, the one medical image I1 is selected from the medical image list in accordance with the instruction of the user which is input from the mouse 105 or the keyboard 106.

In step S505, the attribute information A1 of the medical image I1 is obtained. If the attribute information A1 has been disclosed in the medical image list 210, it is sufficient to read out the attribute information A1 from the list 210. On the other hand, if the attribute information A1 is not disclosed in the medical image list 210, in step S502, the attribute information A1 which is not displayed is also read out simultaneously with the list display items. A second (non-display) medical image list 210' obtained by adding the non-display attribute information A1 to the medical image list 210 is preliminarily formed in the main memory 101. Thus, the attribute information A1 can be read out of the second (non-display) medical image list 210' in the main memory 101.

In step S506, whether or not accurate size information (accurate radiographing range and the height of patient) is included in the attribute information A1 is discriminated. If the accurate size information is included in the attribute information A1, steps S507 and S508 are executed. If it is not included, step S509 is executed.

In step S507, the size of the body diagram of the human body (graphic H1 in the example of FIG. 2) and the size of scale M1 are determined in accordance with the accurate size information included in the attribute information A1. In step S508, the body diagram which has previously been stored in the magnetic disk 102 and the scale M1 are read out and written into the graphic information display area in the display memory 103, thereby displaying the body diagram and the scale M1 onto the monitor 104. In the case of using the display form illustrated in the example of FIG. 3, in next step S510, the type of the body diagram is decided on the basis of the attribute information of the medical image in a manner similar to the case of deciding the type of graphic F1 and the display position. The attribute information which is referred to in this case is information showing the posture of the patient to the bed. The body diagram has several types, such as a face-up position, a face-down position, and a lateral recumbent position.

In step S509, the body diagram which has previously been stored in the magnetic disk 102 (graphic H1 in the example of FIG. 2) is read out and written into the graphic information display area in the display memory 103, thereby displaying the body diagram onto the monitor 104. In the case of using the display form illustrated in the example of FIG. 3, in next step S510, the type of the body diagram is decided on the basis of the attribute information of the medical image in a manner similar to the case of deciding the type of graphic F1 and the display position.

In step S510, the type of graphic F1 and the display position showing the attribute information A1 are decided. As a type of graphic F1, for example, there is a frame line having various display attributes (color, line width, pattern, etc.) or a mask graphic (rectangle having a transmission color, etc.). In the examples of FIGS. 2 and 3, a mask graphic having a mesh pattern is used. The display position of the graphic F1 is determined to a proper position on the body diagram corresponding to the radiographing region of the medical image I1. Since the body diagram (graphic H1) is displayed at a predetermined position (coordinates) in the graphic information display area, it is sufficient that the graphic F1 is also displayed at a predetermined position (coordinates) in accordance with the radiographing region of the medical image I1. The foregoing type of graphic F1 and the display position have been predetermined and stored in the magnetic disk 102. In step S501, they are read out into the main memory 101 at the time of obtaining the list display condition.

In step S511, the graphic F1 decided in step S510 is superimposed and displayed onto the body diagram. In step S511, the graphic F1 or a display effect (background color, color of the frame line, etc.) similar to F1 is drawn in a display area (one row of the list) of the medical image I1 on the medical image list 210. Thus, the display area of the medical image I1 on the medical image list 210 is clarified and the user can understand the attribute information A1 of the medical image I1 at a glance by the graphic F1 on the body diagram.

By the above control procedure, the graphic F1 showing the attribute information A1 of the selected medical image I1 can be displayed at the proper position on the body diagram.

Second Embodiment

In the embodiment, graphics showing attribute information of a plurality of medical images having the same patient ID are simultaneously displayed at the proper positions on the body diagram. Since a constructional example of a display apparatus according to the second embodiment is similar to that in FIG. 1 and has already been described in the first embodiment, its description is omitted here.

Figure 6:
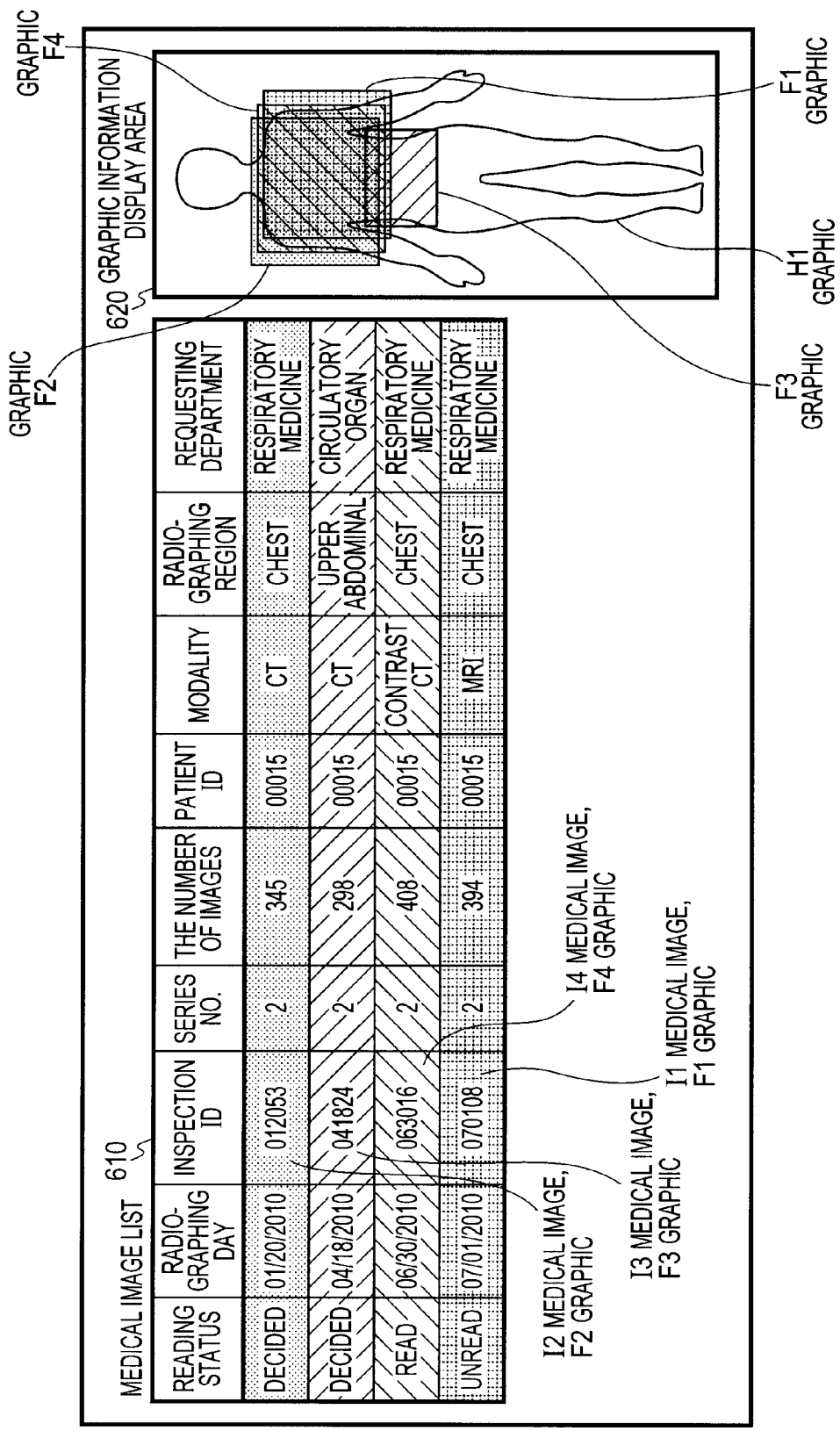
FIG. 6 is a diagram illustrating a display example of a first display screen of a display apparatus according to the second embodiment.

FIG. 6 is a diagram illustrating a display example of a first display screen of the display apparatus according to the second embodiment. Since this diagram has many points similar to those in FIG. 2 in the first embodiment, a description of the points similar to those in FIG. 2 is omitted and only points different from those in FIG. 2 will be described hereinbelow.

In FIG. 6, a medical image list having the same patient ID is displayed on a medical image list 610. By designating a specific patient ID and a range of a radiographing day (for example, within past one year) as a list display condition, the user can obtain the medical image list 610 illustrated in the example of FIG. 6.

The graphic H1 serving as a body diagram of a human body and graphics F1 to Fn showing predetermined attribute information A1 to An of medical images I1 to In having the same patient ID are displayed in a graphic information display area 620. In the example of the drawing, n=4. The graphics F1 to Fn are used as meaning showing the information for graphically displaying the predetermined attribute information A1 to An of the medical images I1 to In. Images or symbols may be used in place of the graphics. In the example of the drawing, the radiographing regions are used as predetermined attribute information A1 to An of the medical images. The graphics F1 to F4 are displayed as rectangles showing the radiographing ranges at positions properly showing the radiographing regions of the medical images I1 to 14, respectively. As mentioned in the first embodiment, if the more accurate radiographing position information can be used in place of the radiographing regions, the graphics F1 to F4 can be displayed at the more accurate positions to the graphic H1 by using those information.

Figure 7:
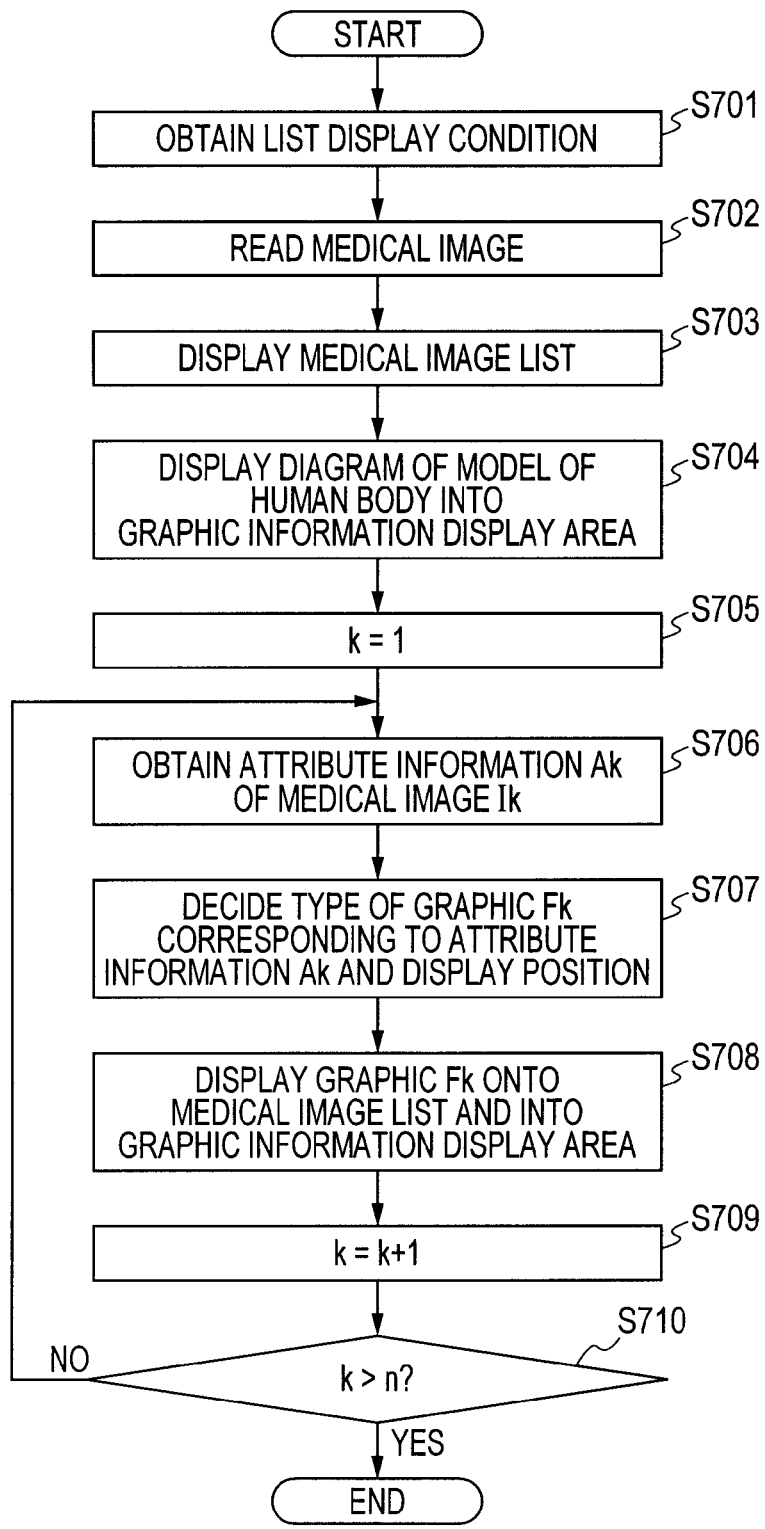
FIG. 7 is a flowchart illustrating a control procedure of the display apparatus according to the second embodiment.

FIG. 7 is a flowchart illustrating a control procedure of the display apparatus according to the second embodiment.

In step S701, a list display condition of the medical image list is obtained. By designating a specific patient ID and a range of a radiographing day (for example, within past one year) as a list display condition, the user can obtain the medical image list 610 illustrated in the example of FIG. 6.

In step S702, the information (list display items) necessary to display the medical image list is read out of the medical image database 2 through the LAN 3 in accordance with the list display condition. In step S703, the information read out in step S702 is edited into a table format and, thereafter, written into the display memory 103, thereby displaying the medical image list onto the monitor 104. In step S704, the body diagram which has previously been stored in the magnetic disk 102 (graphic H1 in the example of FIG. 6) is read out and written into the graphic information display area in the display memory 103, thereby displaying the body diagram onto the monitor 104.

In step S705, a value 1 is substituted into an index k. The index k is used to designate one medical image Ik (k=1~n) among the medical images I1 to In displayed on the medical image list 610. It is assumed that attribute information of the medical image Ik is set to Ak and a graphic showing the attribute information Ak is set to Fk. In step S706, the attribute information Ak of the medical image Ik is obtained.

In step S707, the type and display position of the graphic Fk showing the attribute information Ak are decided. It is now assumed that the graphic Fk is a graphic having display attributes (color, line width, pattern, etc.) of a type different from another graphic Fk' (k'≠k). The display position of the graphic Fk is decided to a proper position on the body diagram corresponding to the radiographing region of the medical image Ik. Since the body diagram (graphic H1) is displayed at a predetermined position (coordinates) in the graphic information display area, it is sufficient that the graphic Fk is also displayed at a predetermined position (coordinates) in accordance with the radiographing region of the medical image Ik.

In step S708, the graphic Fk decided in step S707 is superimposed and displayed onto the body diagram. In step S708, the graphic Fk or a display effect (background color, color of the frame line, etc.) similar to Fk is drawn in a display area (one row of the list) of the medical image Ik on the medical image list 610. Thus, the display area of the medical image Ik on the medical image list 610 is clarified and the user can understand the attribute information Ak of the medical image Ik at a glance by the graphic Fk on the body diagram.

In step S709, a value "1" is added to the index k. In step S710, whether or not the value of the index k is larger than the number (n) of medical images having the same patient ID displayed on the medical image list 610 is discriminated. If k is equal to or less than n, the processing routine is returned to step S706. If k is larger than n, the processing routine is finished.

By the above control procedure, the graphics F1 to Fn showing the attribute information A1 to An of the plurality of medical images I1 to In having the same patient ID can be simultaneously displayed at the proper positions on the body diagram.

Modification

In step S708 in FIG. 7, when the graphic Fk is displayed, by making display control to draw the graphic Fk after the graphic F(k−1) which had previously been drawn was erased, the graphics F1 to Fn can be sequentially displayed on the body diagram while being switched. Further, by repetitively executing the processes of steps S705 to S710 until the instruction is input from the user, the sequential display of the graphics F1 to Fn can be repetitively executed many times.

As described above, according to the display apparatus of the invention, there is such an advantage that by displaying the graphic showing the attribute information of the medical image at the proper position on the body diagram, the accurate radiographing region of the patient and the posture upon radiographing of the patient can be easily discriminated. Further, there is such an advantage that by simultaneously or sequentially displaying the graphics showing the attribute information of the plurality of medical images having the same patient ID at the proper positions on the body diagram, the attribute information of the plurality of medical images of the same patient can be easily discriminated.

Other Embodiments

The invention is also realized by executing the following processes. That is, software (program) for realizing the functions of the embodiments mentioned above is supplied to a system or an apparatus through a network or various kinds of storage media and a computer (or a CPU, MPU, or the like) of the system or apparatus reads out the program and executes the processes corresponding thereto.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-193751, filed Aug. 31, 2010, which is hereby incorporated by reference herein in its entirety.

What is claimed is:

1. A display apparatus comprising:
an obtaining unit configured to obtain information associated with a human body to be examined;
a forming unit configured to form, based on information on an area radiographed by a radiographing apparatus with respect to the human body to be examined included in the information obtained by the obtaining unit, a graphic showing the area radiographed by the radiographing apparatus on a body diagram of the human body to be examined; and
a display control unit configured to control a monitor to display the graphic formed by the forming unit based on a reference point indicating a part of the human body to be examined included in the information obtained by the obtaining unit,
wherein the information obtained by the obtaining unit includes information on a posture of the human body at the time that the human body was radiographed, and wherein the posture is reflected by the body diagram.

2. The apparatus according to claim 1, wherein the information obtained by the obtaining unit further includes information on a height of the human body that was radiographed, and wherein the height is reflected in a size of the body diagram.

3. The apparatus according to claim 2, wherein the display control unit controls the monitor to display a scale showing a size of the graphic such that the size of the body diagram is changeable according to the height of the human body with the scale being fixed.

4. The display apparatus of claim 1, wherein the display control unit controls the monitor to display the body diagram on a display area of the monitor such that the gravitational force applied to the human body is indicated to have a direction from an upper end of the display area toward a lower end of the display area.

5. A display apparatus comprising:
an obtaining unit configured to obtain information associated with a human body to be examined;
a forming unit configured to form, based on information on an area radiographed by a radiographing apparatus with respect to the human body to be examined included in the information obtained by the obtaining unit, a two-dimensional graphic showing the area radiographed by the radiographing apparatus on a body diagram of the human body to be examined, the two-dimensional graphic being different from an image obtained by the radiographing apparatus; and
a display control unit configured to control a monitor to display the two-dimensional graphic formed by the forming unit and the body diagram so that the two-dimensional graphic is superimposed on the body diagram, wherein the two-dimensional graphic is larger than the body diagram in one of two-dimensional directions.

6. The apparatus according to claim 2, wherein the display control unit controls the monitor to display a scale showing a size of the graphic such that the scale is changeable according to the height of the human body with the size of the body diagram being fixed.

* * * * *